(12) United States Patent
Hansen

(10) Patent No.: US 6,646,143 B2
(45) Date of Patent: Nov. 11, 2003

(54) VITAMIN D ANALOGUES

(75) Inventor: Kai Holst Hansen, Herlev (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 103 days.

(21) Appl. No.: 09/787,664

(22) PCT Filed: Jan. 10, 2001

(86) PCT No.: PCT/DK01/00014

§ 371 (c)(1),
(2), (4) Date: Mar. 20, 2001

(87) PCT Pub. No.: WO01/51464

PCT Pub. Date: Jul. 19, 2001

(65) Prior Publication Data

US 2003/0004144 A1 Jan. 2, 2003

Related U.S. Application Data

(60) Provisional application No. 60/174,924, filed on Jan. 10, 2000.

(51) Int. Cl.[7] ............... A61K 31/593; A61K 31/592; C07C 401/00; C07C 463/00

(52) U.S. Cl. ............... 552/653; 552/653; 514/167

(58) Field of Search ............... 552/653; 514/167

(56) References Cited

U.S. PATENT DOCUMENTS

| 4,719,205 A | | 1/1988 | DeLuca et al. | 514/167 |
|---|---|---|---|---|
| 5,373,004 A | | 12/1994 | DeLuca et al. | 514/167 |
| 6,121,469 A | * | 9/2000 | Norman et al. | 552/653 |
| 6,153,605 A | * | 11/2000 | Barbier et al. | 514/167 |

FOREIGN PATENT DOCUMENTS

| EP | 664287 | * | 7/1995 |
|---|---|---|---|
| WO | WO 98/47866 | | 10/1998 |
| WO | 00-64869 | | 11/2000 |

OTHER PUBLICATIONS

Stephen K. Carter et al. (Chemotheray of Cancer, (1981), John Wiley & Sons).*
Lise Binderup et al., Biochemical Pharmacology, vol. 37, No. 5, (1988) pp 889–895.*
Colston et al, Biochem. Pharmacol., 44:2273–2280 (1992).
Mathiasen et al, J. Steroid Biochem. Molec. Biol., 46:365–371 (1993).

* cited by examiner

Primary Examiner—Sabiha Qazi
(74) Attorney, Agent, or Firm—Birch, Stewart, Kolasch & Birch, LLP

(57) ABSTRACT

Compounds of the formula I

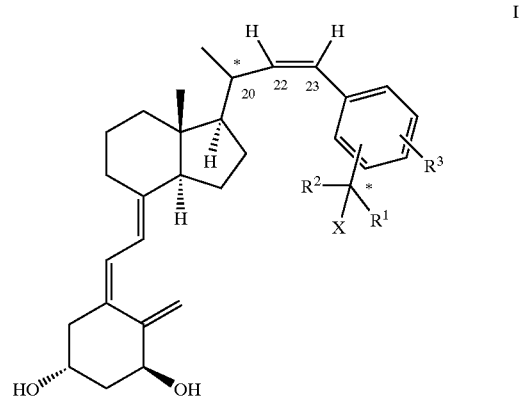

wherein X represents hydrogen or hydroxy; $R^1$ and $R^2$, which may be the same or different, represent hydrogen, $(C_1-C_4)$alkyl optionally substituted with one hydroxyl group or one or more fluorine atoms, or, together with the carbon atom to which they are attached, $R^1$ and $R^2$ form a $(C_3-C_5)$carbocyclic ring; $R^3$ represents $(C_1-C_4)$alkyl, $(C_1-C_4)$alkoxy or a halogen atom, such as fluorine, chlorine, bromine, or iodine, and in-vivo hydrolyzable esters thereof with pharmaceutically acceptable acids, may be used in the prophylaxis and/or treatment of dieases characterized by abnormal cell differentiation and/or cell proliferation.

14 Claims, No Drawings

VITAMIN D ANALOGUES

This application is a 371 of PCT/DK01/00014 filed on Jan. 23, 2003, which claims benefit of 60/174,924 filed on Jan. 10, 2000.

This invention relates to novel vitamin D analogues which show strong activity in inducing differentiation and inhibiting undesirable proliferation of certain cells, including skin cells and cancer cells, as well as immunomodulating effects, to pharmaceutical preparations containing these compounds, to dosage units of such preparations, and to their use in the treatment and prophylaxis of diseases characterized by abnormal cell differentiation and/or cell proliferation.

BACKGROUND OF THE INVENTION

It has been shown that 1α,25-dihydroxy-vitamin $D_3$ (1,25 $(OH)_2D_3$) influences the effects and/or production of interleukins (Muller, K. et al., *Immunol. Lett.,* 17 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that 1,25$(OH)_2D_3$ is able to stimulate the differentiation of cells and inhibit excessive cell proliferation (Abe, E. et al., *Proc. Natl. Acad. Sci.,* U.S.A., 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25$(OH)_2D_3$, or its pro-drug 1α-OH-$D_3$, for the treatment of hypertension (Lind, L. et al., *Acta Med. Scand.,* 222, 423–427 (1987)) and diabetes mellitus (Inomata, S. et al., *Bone Mineral.,* 1, 187–192 (1986)) has been suggested. Another indication for 1,25$(OH)_2D_3$ is suggested by the recent observation of an association between hereditary vitamin D resistance and alopecia: treatment with 1,25$(OH)_2D_3$ may promote hair growth (Editorial, Lancet, March 4, p. 478 (1989)). Also, the fact that topical application of 1,25$(OH)_2D_3$ reduces the size of sebaceous glands in the ears of male Syrian hamsters suggests that this compound might be useful for the treatment of acne (Malloy V. L. et al., The Tricontinental Meeting for Investigative Dermatology, Washington, (1989)).

However, the therapeutic possibilities in such indications are severely limited by the well known potent effect of 1,25$(OH)_2D_3$ on calcium metabolism; elevated blood concentrations will rapidly give rise to hypercalcemia. Thus, this compound and some of its potent synthetic analogues are not satisfactory for use as drugs in the treatment of e.g. psoriasis, leukemia or immune diseases which may require continuous administration of the drug in relatively high doses.

A number of vitamin D analogues have recently been described that show some degree of selectivity in favour of the cell differentiation inducing/cell proliferation inhibiting activity in vitro as compared with the effects on calcium metabolism in vivo (as measured in increased serum calcium concentration and/or increased urinary calcium excretion), which adversely limit the dosage that can safety be administered. One of the first of these to appear, calcipotriol (INN) or calcipotriene (USAN), has been developed on the basis of this selectivity and is now recognized worldwide as an effective and safe drug for the topical treatment of psoriasis.

A study with another vitamin D analogue, Seocalcitol [1(S), 3(R)-dihydroxy20(R)-(5'-ethyl-5'-hydroxy-hepta-1 '(E), 3 '(E)-diene-1'-yl)-9,10-secopregna-5(Z), 7(E), 10(19)-triene], selected on this basis supports the concept that systemically administered vitamin D analogues may inhibit breast cancer cell proliferation in vivo at sub-toxic doses (Colston, K. W. et al., *Biochem. Pharmacol.* 44, 2273–2280 (1992) and Mathiasen, I. S. et al., *J. Steroid Biochem. Molec. Biol.,* 46, 365–371 (1993)).

Related compounds having the following formula are disclosed in WO 98/47866:

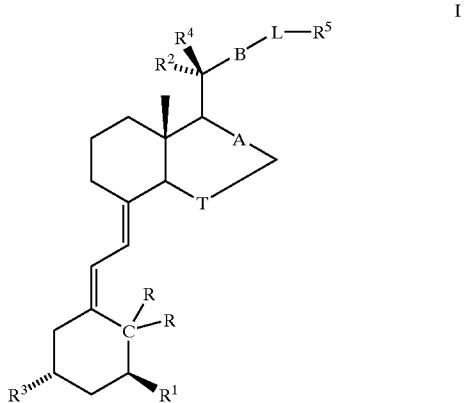

wherein A is a single or double bond, T is $CH_2$ or $CH_2CH_2$; B is $CH_2CH_2$, CH=CH or C≡C, $R^1$ and $R^3$ are H or OH, C(R,R) is $CH_2$ or C=$CH_2$, $R^2$ is $CH_3$ and $R^4$ is H, or $R^2$ is H and $R^4$ is $CH_3$, L is phenyl and $R^5$ is OH or C($C_{1-4}$-alkyl)$_2$ OH, or L—$R^5$ is 2-furyl which is 5-substituted by C(($C_{1-4}$-alkyl)$_2$OH, with the proviso that when L is phenyl, A is a single bond, B is C≡C, T is $CH_2$, each $R^1$ and $R^3$ are OH, C(R,R) is C=$CH_2$, $R^2$ is $CH_3$, $R^4$ is H, and $R^5$ is C)$CH_3)_2$ OH, then $R^5$ must be in position ortho or para. These compounds are described in WO 98/47866 as useful in the treatment or prevention of vitamin D dependent disorders, particularly psoriasis, basal cell carcinomas, disorders of keratinization and keratosis, leukemia, osteoporosis, hyperparathyroidism accompanying renal failure, transplant rejection and graft vs. host disease.

The stereochemistry of the compounds described in WO 98/47866 is not given at the double bond (position 22) when B is CH=CH. However, from the exemplification and the syntheses which are disclosed, it is evident that only 22-trans compounds are envisaged.

Notwithstanding the extensive prior art efforts to provide therapeutically effective products, there is a continuing need for new vitamin D analogues with an acceptable combination of desired therapeutic activity and minimum toxic effects. The compounds of the present invention provide hitherto undisclosed vitamin D analogues with cell proliferation inhibitory and cell differentiating promoting activities without the undesired side effects of increased serum calcium levels and skin irritation.

SUMMARY OF THE INVENTION

The present invention relates to compounds of the general formula I

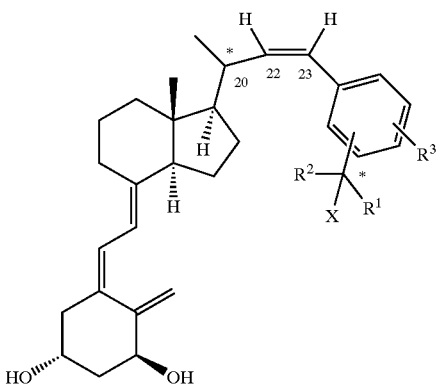

wherein X represents hydrogen or hydroxy; $R^1$ and $R^2$, which may be the same or different, represent hydrogen, $(C_1-C_4)$alkyl optionally substituted with one hydroxyl group or one or more fluorine atoms, or, together with the carbon atom to which they are attached, $R^1$ and $R^2$ form a $(C_3-C_5)$carbocyclic ring. $R^3$ represents hydrogen, $(C_1-C_4)$ alkyl, $(C_1-C_4)$alkoxy, or a halogen atom, such as fluorine, chlorine, bromine, or iodine.

The configuration of the carbon atoms marked with an asterisk may be both S or R.

The present invention also relates to in vivo hydrolyzable esters of the compounds of general formula I with pharmaceutically acceptable acids.

As will be evident, the compounds of formula I have the cis-configuration at the double bond at position 22. According to the invention, it has been found that the 22-cis compounds are much more active in stimulating cell differentiation and inhibiting undesirable cell proliferation.

DETAILED DESCRIPTION OF THE INVENTION

Preferred Embodiments

In compounds of the invention it is preferred that X represents hydroxy; $R^1$ and $R^2$ are the same and preferably represent $(C_1-C_2)$alkyl optionally substituted with one hydroxyl group or one or more fluorine atoms; and $R^3$ represents hydrogen,$(C_1-C_2)$alkyl, fluorine or chlorine. Preferred positions of the $C(R^1)(R^2)(X)$ group are meta and para. Even more preferred are compounds of formula I wherein $R^1$ and $R^2$ both represent methyl, trifluoromethyl, or ethyl, and $R^3$ represents hydrogen.

The invention also includes diastereoisomers of the compounds of formula I in pure form or as a mixture of diastereoisomers of a compound of formula I.

Preferred compounds of the invention are selected from the group consisting of:

1(S), 3(R)-Dihydroxy-20(R)-[2(Z)-(3-(2-hydroxy-2-propyl)-phenyl)-vinyl]-9, 10-secopregna-5(Z), 7(E), 10(19)-triene.

1(S), 3(R)-Dihydroxy-20(S)-[2(Z)-(4-(2-hydroxy-2-propyl)-phenyl)-vinyl]-9,10-secopregna-5(Z), 7(E), 10(19)-triene.

1(S), 3(R)-Dihydroxy-20(R)-[2(Z)-(4-(2-hydroxy-2-propyl)-phenyl)-vinyl]-9,10-secopregna-5(Z), 7(E), 10(19)-triene, and in-vivo hydrolyzable esters thereof with pharmaceutically acceptable acids.

The term "alkyl" as used herein refers to any univalent group derived from an alkane by removal of a hydrogen atom from any carbon atom, and includes the subclasses of normal alkyl (n-alkyl), and primary, secondary and tertiary alkyl groups respectively, and having the number of carbon atoms specified, including for example methyl, ethyl, n-propyl, i-propyl, n-butyl, sec. butyl, tert. butyl and isobutyl. Alkane refers to an acyclic branched or unbranched hydrocarbon having the general formula $C_nH_{2n+2}$, and therefore consisting entirely of hydrogen atoms and saturated carbon atoms.

"Halogen" is intended to indicate fluoro, chloro, bromo or iodo; fluoro, chloro, and bromo being preferred

Synthesis, Reactions

The Compounds of the invention may be prepared as outlined in Scheme Ia. Coupling of an alkyne of formula 1a (Calverley, M. J. and Bretting, C. Aa. S.; Bioorg. Med. Chem. Lett. 9 1841–1844 1993) to an arylic side chain fragment of formula II in the presence of catalytic amounts of a palladium complex such as $Pd(PPh_3)_4$ or $Pd(PPh_3)_2Cl_2$, catalytic amounts of copper (I) iodide and an organic amine base as solvent, gives an intermediate of formula IIIa. The 22-triple bond in IIIa is reduced to a 22- cis-double bond with hydrogen in the presence of catalytic amounts of a Lindlar catalyst.

The conversion of the intermediate IVa to Ia involves a photoisomerisation step and a deprotection step, analogous to the steps used in last stages of the synthesis of other vitamin D analogues, cf. EP patent No. 0 227 826.

The compounds of formula Ib (20-epimers of Ia) are prepared analogously with the 20-epimer 1b (Bretting C, Mørk Hansen C, Rastrup Andersen N 1994 Chemistry and biologi of 22,23-yne analogs of calcitriol. In: Norman A W, Bouillon R, Thomasset M (eds.) Vitamin D —A Pluripotent Steroid Hormone: Structural Studies, Molecular Endocrinology and Clinical Applications. Walter de Gruyter, Berlin-N.Y., pp.73–74) as starting material as outlined in Scheme Ib.

The side chain building blocks of formula II are either known compounds or may be prepared as outlined in Scheme II.

Alternatively the compounds of the invention may be prepared as outlined in Scheme III. A vitamin D analogue of formula 2b (Calverley M. J., Tetrahedron, 43, 4609, (1987)) with an aldehyde carbonyl in position 22 reacts with an alkylidene phosphorane of formula X to give a mixture of a 22(Z) and a 22(E) isomers from which the 22(Z) isomer IV is isolated by chromatography.

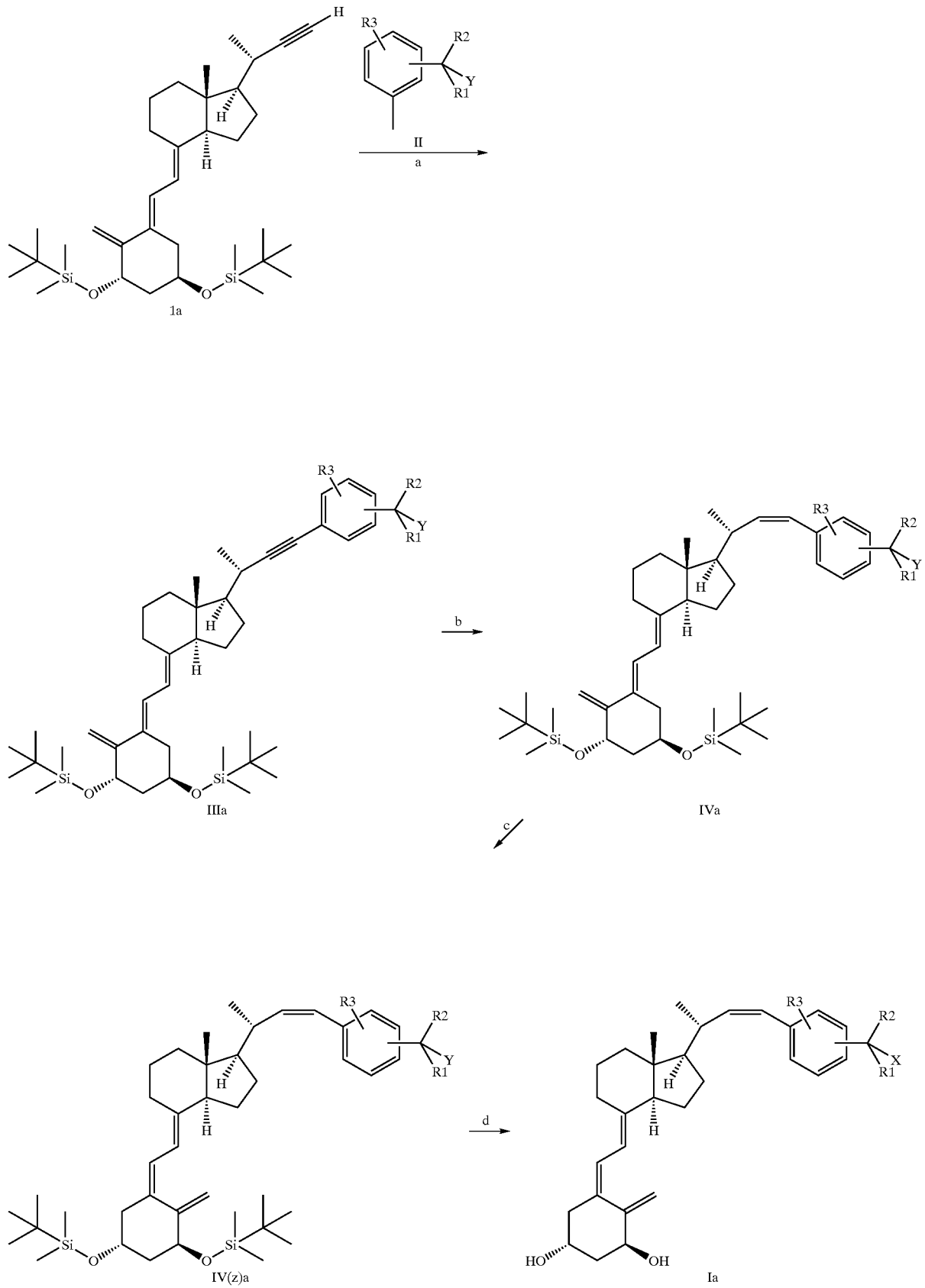

Scheme Ib
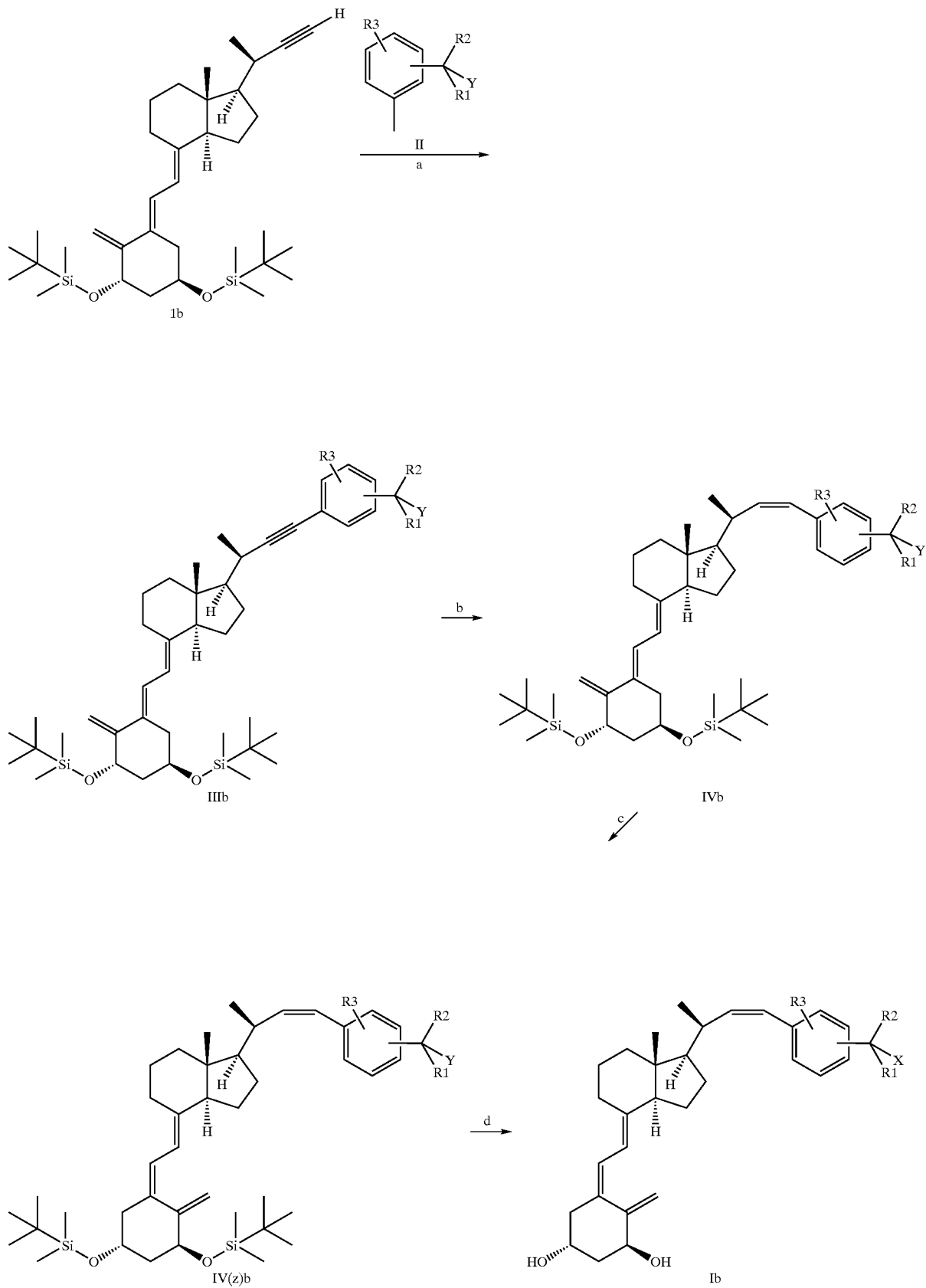

Notes to scheme Ia and Ib:

X1 is bromine or iodine

Y is hydrogen, hydroxy or a protected hydroxy group

X, $R^1$, $R^2$ and $R^3$ are as defined above.

a) Heck coupling with $Pd(PPh_3)_2Cl_2$/copper(I) iodide as catalyst.
b) Hydrogenation in the presence of a Lindlar catalyst.
c) Isomerisation with hv in the presence of a triplet sensitizer, e.g. anthracene.
d) Deprotection with TBAF or HF.

Scheme II

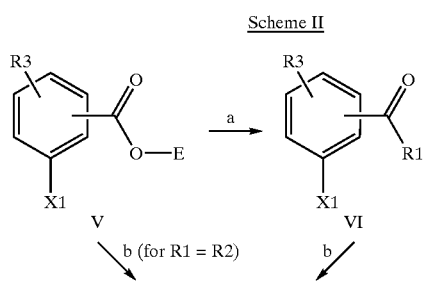

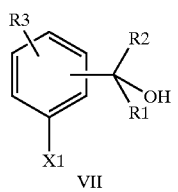

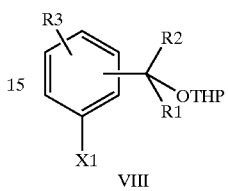

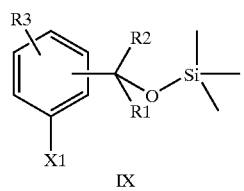

Notes to scheme II:

E is lower alkyl such as methyl, ethyl or isopropyl
$X^1$, $R^1$, $R^2$ and $R^3$ are as defined above.
a) Grignard reaction with $R^1MgBr$ or $R^1MgI$.
b) Grignard reaction with $R^2MgBr$ or $R^2MgI$.
c) Reaction with dihydropyran.
d) Silylation with $Me_3SiCl$ + base.

Scheme III

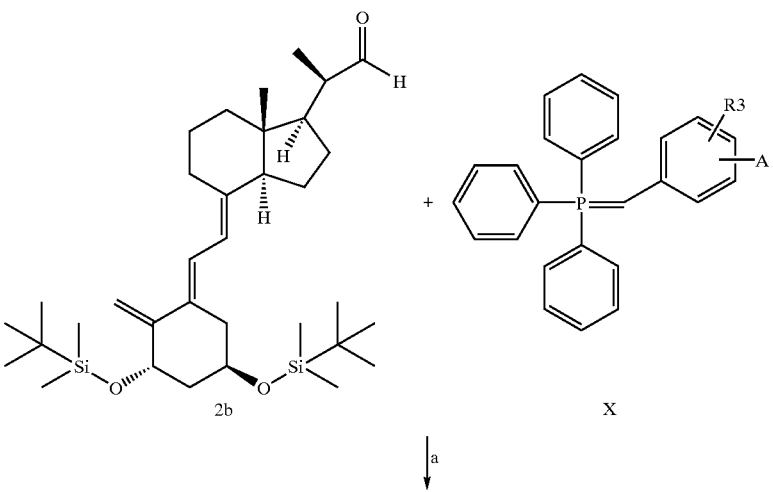

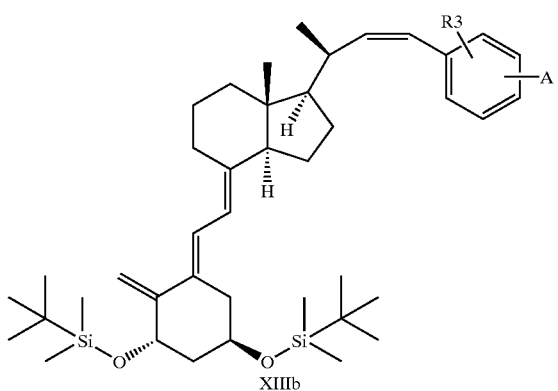

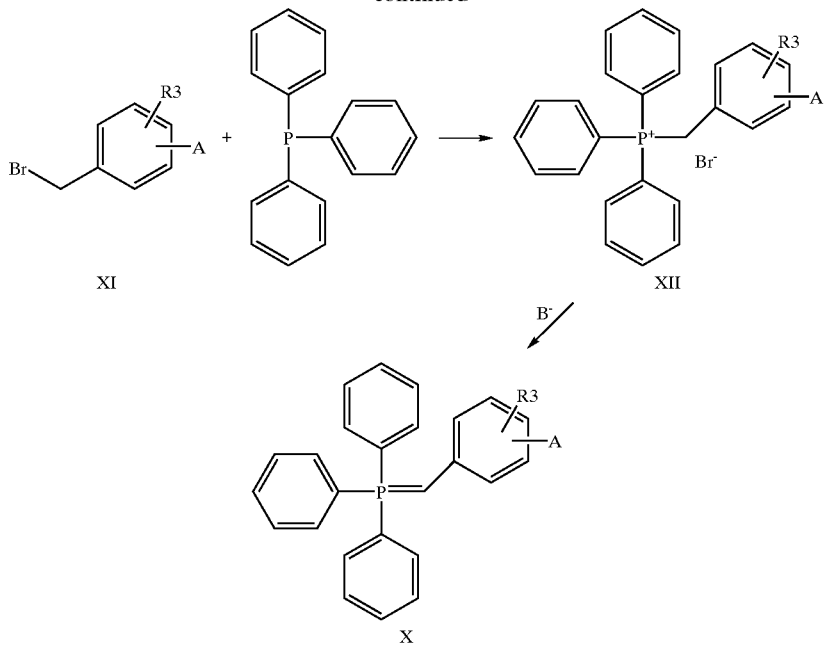

Notes to scheme III:
R³ is as defined above
A is a group "C(R¹)(R²)(Y)", where R¹, R², and Y are as defined above, or a group that easily may be converted to "C(R¹)(R²)(Y)" e.g. an ester group.
a) Wittig reaction (The alkylidene phosphorane X is prepared in situ by action of a base on the easily accessible triphenylalkylphosphoniun halide XII.)

The following standard abbreviations are used throughout this disclosure: $Bu^t$=tert-butyl, DMF=N,N-dimethylformamide, DMAP=4-dimethylaminopyridine Et=ethyl, Ether=diethyl ether, pet.ether=petroleum ether, Me=methyl, PPTS=pyridinium p-toluenesulfonate, Py=pyridine, TBAF=tetra-n-butylammonium fluoride, TBS=tert-butyldimethylsilyl, THF=tetrahydrofuran, THP=tetrahydro-4H-pyran-2-yl, Ts=tosyl.

Pharmacological Methods

In order to demonstrate the effectiveness of the compounds of formula I an assay for the rating of test compounds for antiproliferative activity in skin cells, e.g. antipsoriatic effect, such as the in vitro assay using HaCaT, a spontaneously immortalized, non-tumorigenic human skin keratinocyte cell line (Mørk Hansen, C. et al., *J. Invest. Dermatol.* 1, 44–48 (1996)), measuring $^3$H-thymidine uptake can be used.

Generally, the classical effects of $1,25(OH)_2D_3$ on the calcium balance in the organism, including calcemic and calciuric activities, are unwanted in the vitamin D analogues of the present invention, in which selectivity for e.g. inhibition of the proliferation of certain cells, absence of calcemic effects and skin irritation is desired. Thus, the calcemic activity of the compounds may be determined in rats in vivo, as previously described (Binderup, L., Bramm, E., Biochem. Pharmacol. 37, 889–895 (1988)).

Furthermore, the binding to the vitamin D receptor relative to the binding of Calcitriol of the present compounds compared to compounds of the prior art may be determined in vitro as previously described (Binderup, L., Bramm, E., Biochem. Pharmacol. 37, 889–895 (1988)).

The present compounds are intended for use in pharmaceutical compositions which are useful in the local or sytemic treatment of human and veterinary disorders such as cancer, leukemia, myelofibrosis, and psoriasis, of a number of disease states including hyperparathyroidism, particularly secondary hyperparathyroidism associated with renal failure, diabetes mellitus, hypertension, acne, alopecia, skin ageing, AIDS, neurodegenerative disorders such as Alzheimer's disease, host versus graft reactions, rejection of transplants, for prevention and/or treatment of steroid induced skin atrophy, and for promoting osteogenesis and treating osteoporosis.

The present compounds may be used in combination with other pharmaceuticals or treatment modalities. In the treatment of psoriasis the present compounds may be used in combination with other antipsoriatic drugs, e.g. steroids, or with other treatments e.g. light- or UV-light-treatment or the combined PUVA-treatment. In the treatment of cancer the present compounds may be used in combination with other anti-cancer drugs or anti-cancer treatments, such as radiation treatment. In the prevention of graft rejection and graft versus host reaction, or in the treatment of auto-immune diseases, the present compounds may advantageously be used in combination with other immunosuppressive/immunoregulating drugs or treatments, e.g. with cyclosporin A.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

The formulations, both for veterinary and for human medical use, of the present invention thus comprise an active ingredient in association with a pharmaceutically acceptable carrier therefore and optionally other therapeutic ingredient (s). The carrier(s) must be "acceptable" in the sense of being compatible with the other ingredients of the formulations and not deleterious to the recipient thereof.

The formulations include e.g. those in a form suitable for oral, ophthalmic, rectal, parenteral (including subcutaneous, intramuscular and intravenous), transdermal, intra-articular and topical administration.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient which is preferably isotonic with the blood of the recipient. Transdermal formulations may be in the form of a plaster or a patch.

Formulations suitable for intra-articular or ophthalmic administration may be in the form of a sterile aqueous preparation of the active ingredient which may be in microcrystalline form, e.g. in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

In addition to the aforementioned ingredients, the formulations of this invention may include one or more additional ingredients, such as diluents, binders, preservatives etc.

The compositions may further contain other therapeutically active compounds usually applied in the treatment of the above mentioned pathological conditions, such as other immunosuppressants in the treatment of immunological diseases, or steroids in the treatment of dermatological diseases.

The present invention further concerns a method for treating patients suffering from one of the above pathological conditions, said method consisting of administering to a patient in need of treatment an effective amount of one or more compounds of formula I, alone or in combination with one or more excipients or other therapeutically active compounds usually applied in the treatment of said pathological conditions. The treatment with the present compounds and/or with further therapeutically active compounds may be simultaneous or with intervals.

In the systemic treatment daily doses of from 0.001–2 $\mu$g per kilogram bodyweight, preferably from 0.002–0.3 $\mu$g/kg of mammal bodyweight, for example 0.003–0.3 $\mu$g/kg of a compound of formula I are administered, typically corresponding to a daily dose for an adult human of from 0.2 to 25 $\mu$g. In the topical treatment of dermatological disorders, ointments, creams or lotions containing from 0.1–1000 $\mu$g/g, and preferably from 1–500 $\mu$g/g, and more preferably from 10–250 $\mu$g/g, of a compound of formula I are administered. For topical use in ophthalmology ointments, drops or gels containing from 0.1–1000 $\mu$g/g, and preferably from 1–500 $\mu$g/g, more preferably from 10–250 $\mu$g/g, of a compound of formula I are administered. The oral compositions are formulated, preferably as tablets, capsules, or drops, containing from 0.05–100 $\mu$g, preferably from 0.1–50 $\mu$g, of a compound of formula I, per dosage unit.

The invention will now be further described in the following General Procedures, Preparations and Examples

EXAMPLES

General

The exemplified compounds of formula I are listed in Table 1, whereas intermediates of formula VII; VIII; and IX are listed in Table 2, and intermediates of formula III and IV are listed in Table 3.

For nuclear magnetic resonance spectra (300 MHz) chemical shift values ($\delta$) are quoted for deuteriochloroform solutions relative to internal tetramethylsilane ($\delta$=0) or chloroform ($\delta$=7.25). The value for a multiplet, either defined (doublet (d), triplet (t), quartet (q)) or not (m) at the approximate mid point is given unless a range is quoted (s=singlet, b=broad).

Coupling constants (J) are given in Hertz (Hz), and are sometimes approximated to the nearest unit.

Ether is diethyl ether, and was dried over sodium. THF was dried over sodium-benzophenone. Petroleum ether refers to the pentane fraction. Reactions were routinely run under an argon atmosphere at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

TABLE 1

Exemplified Compounds of Formula I

| Compound No. | Ex. No. | Config. | Pos. of *) | $R^1$ | $R^2$ | $R^3$ | X |
|---|---|---|---|---|---|---|---|
| 101 | 1 | 20(R) | 3 | Me | Me | H | OH |
| 102 | 2 | 20(S) | 4 | Me | Me | H | OH |
| 103 | 3 | 20(R) | 4 | Me | Me | H | OH |
| 104 | | 20(S) | 3 | Me | Me | H | H |
| 105 | | 20(R) | 4 | Me | Me | H | H |
| 106 | | 20(S) | 3 | Et | Et | H | OH |
| 107 | | 20(R) | 3 | Et | Et | H | OH |
| 108 | | 20(R) | 4 | Me | Me | 2-Cl | OH |
| 109 | | 20(S) | 4 | Et | Et | 2-F | OH |
| 110 | | 20(R) | 4 | Me | Me | 2-OCH$_3$ | OH |
| 111 | | 20(S) | 4 | Me | Me | 2-Me | OH |
| 112 | | 20(S) | 3 | Me | Me | 5-Cl | OH |
| 113 | | 20(S) | 3 | Me | Me | 5-F | OH |
| 114 | | 20(R) | 3 | Et | Et | 5-OCH$_3$ | OH |
| 115 | | 20(S) | 3 | Me | Me | 5-Me | OH |
| 115 | | 20(S) | 3 | Me | Me | 5-isopr. | OH |
| 116 | | 20(S) | 3 | Et | Et | 6-Cl | OH |
| 117 | | 20(S) | 3 | Me | Me | 6-F | OH |
| 118 | | 20(R) | 3 | Et | Et | 6-OCH$_3$ | OH |
| 119 | | 20(S) | 3 | Me | Me | 6-OEt | OH |
| 120 | | 20(S) | 3 | Me | Me | 6-Me | OH |
| 121 | | 20(S) | 3 | Me | Me | 6-Et | OH |
| 122 | | 20(S) | 3 | Me | Me | 6-isopr. | OH |

*) = —C($R^1$)($R^2$)(X)

TABLE 2

Non-limiting Examples of Intermediates of Formulas VII, VIII and IX

| Preparation No. | Compound No. | GP **) | Formula | X1 | R1 | R2 | R3 |
|---|---|---|---|---|---|---|---|
| 1 | 3 | 1 | VII | 4-I | Me | Me | H |
| 2 | 4 | 1 | VII | 3-I | Me | Me | H |
| 3 | 5 | 2 | VIII | 4-I | Me | Me | H |
| 4 | 6 | 2 | VIII | 3-I | Me | Me | H |
| 5 | 7 | 3 | IX | 4-I | Me | Me | H |
| | 8 | 1a | VII | 3-I | Et | Et | H |
| | 9 | 2 | VIII | 3-I | Et | Et | H |
| | 10 | 1 | VII | 4-I | Me | Me | 5-Cl |
| | 11 | 2 | VIII | 4-I | Me | Me | 5-Cl |
| | 12 | 1a | VII | 4-Br | Et | Et | 5-F |
| | 13 | 3 | IX | 4-Br | Et | Et | 5-F |
| | 14 | 1 | VII | 4-Br | Me | Me | 5-OMe |
| | 15 | 2 | VIII | 4-Br | Me | Me | 5-OMe |
| | 16 | 1 | VII | 4-I | Me | Me | 5-Me |
| | 17 | 3 | IX | 4-I | Me | Me | 5-Me |
| | 18 | 1 | VII | 3-Br | Me | Me | 5-Cl |
| | 19 | 2 | VIII | 3-Br | Me | Me | 5-Cl |
| | 20 | 1 | VII | 3-Br | Me | Me | 5-F |
| | 21 | 2 | VIII | 3-Br | Me | Me | 5-F |
| | 22 | 1a | VII | 3-I | Et | Et | 5-OMe |
| | 23 | 2 | VIII | 3-I | Et | Et | 5-OMe |
| | 24 | 1 | VII | 3-I | Me | Me | 5-Me |
| | 25 | 2 | VIII | 3-I | Me | Me | 5-Me |
| | 26 | 1 | VII | 3-Br | Me | Me | 5-iPr |
| | 27 | 2 | VIII | 3-Br | Me | Me | 5-iPr |
| | 28 | 1a | VII | 3-I | Et | Et | 4-Cl |
| | 29 | 2 | VIII | 3-I | Et | Et | 4-Cl |
| | 30 | 1 | VII | 3-I | Me | Me | 4-F |
| | 31 | 2 | VIII | 3-I | Me | Me | 4-F |
| | 32 | 1a | VII | 3-I | Et | Et | 4-OCH$_3$ |
| | 33 | 2 | VIII | 3-I | Et | Et | 4-OCH$_3$ |
| | 34 | 1 | VII | 3-I | Me | Me | 4-OEt |
| | 35 | 2 | VIII | 3-I | Me | Me | 4-OEt |
| | 36 | 1 | VII | 3-I | Me | Me | 4-Me |
| | 37 | 2 | VIII | 3-I | Me | Me | 4-Me |
| | 38 | 1 | VII | 3-I | Me | Me | 4-Et |
| | 39 | 2 | VIII | 3-I | Me | Me | 4-Et |
| | 40 | 1 | VII | 3-I | Me | Me | 4-iPr |
| | 41 | 2 | VIII | 3-I | Me | Me | 4-iPr |

**) = General Procedure

TABLE 3

Non-limiting examples of intermediates of formulas III and IV

| Compound No. | Prep. No. | Formula | Pos. of ***) | $R^1$ | $R^2$ | Y | $R^3$ |
|---|---|---|---|---|---|---|---|
| 42 | 6 | IVb | 4 | Me | Me | OH | H |
| 43 | 7 | IV(z)b | 4 | Me | Me | OH | H |
| 44 | 8 | IIIa | 4 | Me | Me | OTHP | H |
| 45 | 9 | IIIa | 4 | Me | Me | OH | H |
| 46 | 10 | IVa | 4 | Me | Me | OH | H |
| 47 | 11 | IV(z)a | 4 | Me | Me | OH | H |
| 48 | 12 | IVa | 3 | | COOMe | | H |
| 49 | 13 | IV(z)a | 3 | | COOMe | | H |
| 50 | 14 | IV(z)a | 3 | Me | Me | OH | H |
| 51 | | IIIb | 3 | Me | Me | H | H |
| 52 | | IVb | 3 | Me | Me | H | H |
| 53 | | IIIa | 4 | Me | Me | H | H |
| 54 | | IVa | 4 | Me | Me | H | H |
| 55 | | IIIb | 3 | Et | Et | OH | H |
| 56 | | IVb | 3 | Et | Et | OH | H |
| 57 | | IIIa | 3 | Et | Et | OH | H |
| 58 | | IVa | 3 | Et | Et | OH | H |
| 59 | | IIIa | 4 | Me | Me | OH | 2-Cl |
| 60 | | IVa | 4 | Me | Me | OH | 2-Cl |
| 61 | | IIIb | 4 | Et | Et | OH | 2-F |
| 62 | | IVb | 4 | Et | Et | OH | 2-F |
| 63 | | IIIa | 4 | Me | Me | OH | 2-OMe |
| 64 | | IVa | 4 | Me | Me | OH | 2-OMe |
| 65 | | IIIb | 4 | Me | Me | OH | 2-Me |
| 66 | | IVb | 4 | Me | Me | OH | 2-Me |
| 67 | | IIIb | 3 | Me | Me | OH | 5-Cl |
| 68 | | IVb | 3 | Me | Me | OH | 5-Cl |
| 69 | | IIIb | 3 | Me | Me | OH | 5-F |
| 70 | | IVb | 3 | Me | Me | OH | 5-F |
| 71 | | IIIa | 3 | Et | Et | OH | 5-OMe |
| 72 | | IVa | 3 | Et | Et | OH | 5-OMe |
| 73 | | IIIb | 3 | Me | Me | OH | 5-Me |
| 74 | | IVb | 3 | Me | Me | OH | 5-Me |
| 75 | | IIIb | 3 | Me | Me | OH | 5-iPr |
| 76 | | IVb | 3 | Me | Me | OH | 5-iPr |
| 77 | | IIIb | 3 | Et | Et | OH | 6-Cl |
| 78 | | IVb | 3 | Et | Et | OH | 6-Cl |
| 79 | | IIIb | 3 | Me | Me | OH | 6-F |
| 80 | | IVb | 3 | Me | Me | OH | 6-F |
| 81 | | IIIa | 3 | Et | Et | OH | 6-OMe |
| 82 | | IVa | 3 | Et | Et | OH | 6-OMe |
| 83 | | IIIb | 3 | Me | Me | OH | 6-OEt |
| 84 | | IVb | 3 | Me | Me | OH | 6-OEt |
| 85 | | IIIb | 3 | Me | Me | OH | 6-Me |
| 86 | | IVb | 3 | Me | Me | OH | 6-Me |
| 87 | | IIIb | 3 | Me | Me | OH | 6-Et |
| 88 | | IVb | 3 | Me | Me | OH | 6-Et |
| 89 | | IIIb | 3 | Me | Me | OH | 6-iPr |
| 90 | | Ivb | 3 | Me | Me | OH | 6-iPr |

***) = —C($R^1$)($R^2$)(Y)

General Procedures

General procedure 1

Reaction of Methyl Magnesium Iodide with an Ester of Formula V

To a stirred ice-cooled solution of the methyl ester V (27 mol) in dried ether (20 ml) is added dropwise over 20 minutes a filtered solution of a Grignard reagent, prepared from magnesium (1.47 g, 60 mmol) and methyl iodide (4.0 ml, 64 mmol) in dried ether (40 ml). After stirring for two hours at room temperature, water (40 ml) is slowly poured into the reaction mixture. The phases are separated, and the aqueous phase is extracted with ether (3×50 ml). The combined ether phases are consecutively extracted with 1 N aqueous HCl (50 ml water (3×50 ml), and saturated aqueous sodium chloride (50 ml ), dried over MgSO$_4$ and concentrated in vacuo to yield a dark oil. The crude oil is purified by chromatography on silica gel to give the ketone of formula VI as a minor product and the alcohol of formula VII as the major product. The compound of formula VII may if convenient be crystallised from hexane or from a mixture of hexane and ether.

Variation

General Procedure 1a

The procedure of General Procedure 1 was followed, except that ethyl bromide is used instead of methyl iodide.

General Procedure 2

Preparation of a Tetrahydro-4H-pyran-2-yl-ether of Formula VIII

An alcohol of formula VII (16 mmol) is dissolved in methylene chloride(50 ml), 3,4-dihydro-2H-pyran (2.4 ml, 26 mmol) and pyridinium p-toluene sulfonate (0.43 g, 1,7 mmol) are added, and the mixture is stirred at room temperature for 4 hours. The reaction mixture is diluted with ether (150 ml) and extracted with water (3×50 ml) and saturated aqueous sodium chloride (50 ml), dried and concentrated in vacuo. The crude product is purified by chromatography on silicagel.

General Procedure 3

Preparation of a Trimethylsilylether of Formula IX

To a solution of a compound of formula VII (14 mmol) in dry dichloromethane (50 ml) triethylamine (42 mmol) and DMAP (25 mg) are added under argon and with stirring and cooling in an ice bath. Trimethylsilyl chloride (40 mmol) is added dropwise with stirring during 20 minutes at 0° C., and stirring is continued for 2–6 hours at room temperature. Ether (500 ml) and water (100 ml) are added. The organic phase is isolated, extracted with water (3×50 ml), and saturated aqueous sodium chloride (50 ml ), dried and concentrated in vacuo. The residue is purified by chromatography on silica gel to give the desired product as a yellowish oil.

General Procedure 4

Heck Coupling of Compound 1 and a Side Chain Fragment of Formula II

Compound 1 (100 mg, 0.17 mmol), a compound of formula II (0.2 mmol), bis(triphenylphosphine)palladium (II) dichloride (24 mg), and copper(I) iodide are dissolved in a mixture of dry triethylamine (5 ml) and dry THF (4 ml) and stirred under argon overnight. The reaction mixture is quenched with water (15 ml) and diluted with ether (85 ml). The organic phase is isolated, extracted with water (3×15 ml), and saturated aqueous sodium chloride (15 ml), dried and concentrated in vacuo. The residue is purified by chromatography on silica gel (eluant: 1–5% ether in pentane) to give the desired product as an amorphous gum.

General Procedure 5

Hydrogenation in the Presence of a Lindlar Catalyst

A compound of formula III (0.57 mmol) is dissolved in a mixture of dichloromethane (5 ml) and ethanol (20 ml) Lindlar catalyst (100 mg) is added and mixture is stirred under hydrogen until the consumption of hydrogen has ceased. The catalyst is filtered off and the filtrate is diluted with ethyl acetate (80 ml). The organic phase is extracted with water (3×15 ml), and saturated aqueous sodium chloride (15 ml), dried and concentrated. The residue is purified by chromatography on silica gel (eluant: 1–5% ether in pentane) to give the desired product as an amorphous gum.

General Procedure 6

Isomerization of a Compound of Formula IV to the Corresponding 5(Z) Isomer

A solution of the appropriate compound of formula IV (0.3 mmol), anthracene (100 mg) and triethylamine (0.05 ml) in dichloromethane (20 ml) under argon in a Pyrex flask is irradiated with UV-light from a high pressure ultraviolet lamp, type TQ760 Z2 (Hanau) at about 10° C. for 20 minutes under stirring. The reaction mixture is concentrated in vacuo and treated with pet. ether (2×5 ml). After filtering the filtrate is concentrated in vacuo and purified by chromatography (mixture of ether and pet. ether as eluant) to yield the title compound of the preparation.

General Procedure 7

Wittig Reaction with a Carbonyl Compound of Formula 2b

The triphenylalkylphosphonium halide (XII) (1.2 mmol) is dissolved in dichloromethan (10 ml). Under argon 2N sodium methanolate (1.2 ml) and 1(S), 3(R)-bis-(tert-butyldimethylsilyloxy)-20(R) formyl-9,10-secopregna-5 (E), 7(E), 10(19)-triene (2b)(1 mmol) are added. The reaction mixture is stirred under argon overnight and the deep orange colour faded to yellow.

The reaction mixture is diluted with ether (25 ml) and extracted with water (2×10 ml), dried and concentrated to give a mixture of the 22-cis and the 22-trans isomer as a yellow oil. The 22-cis isomer is isolated by chromatography on silica gel (mixture of ether and petroleum ether as eluant).

General Procedure 8

Preparation of a Triphenylalkylphosphonium Halide of Formula XII

Triphenylphosphine (2.62 g, 20 mmol) and a bromide of formula XI (20 mmol) are dissolved in benzene (12 ml) and stirred over night at room temperature. The precipitate is filtered off, washed with benzene (5×2 ml) and petroleum ether (5 ml) and dried in vacuo to yield a triphenylalkylphosphonium halide of formula XII.

General Procedure 9

Deprotection with HF

To a stirred solution of the appropriate silyl-protected compound of formula IV(z) (0.25 mmol) in ethyl acetate (1.5 ml) is added acetonitrile (6 ml) followed by a 5% solution of hydrofluoric acid in acetonitrile-$H_2O$ 7:1 (2.0 ml). After stirring for a further 45–60 minutes, 1 M potassium hydrogen carbonate (10 ml) is added, and the reaction mixture is worked up (ethyl acetate). The residue is purified by chromatography (eluant: 30% pentane in ethyl acetate) to give the desired compound of formula I.

General Procedure 10

Deprotection with TBAF

To a solution of the appropriate silyl-protected compound of formula IV(z) (0.18 mmol) in THF (4.5 ml) is added TBAF trihydrate (0.29 g, 0.9 mmol), and the mixture is heated to reflux for one hour with stirring. After addition of 0.2 M sodium hydrogen carbonate (5 ml), the mixture is worked up (ethyl acetate). The residue is purified by chromatography (eluant: 30% pentane in ethyl acetate) to yield the desired compound of formula I.

General Procedure 11

Reaction of Methyl Lithium with an Ester of Formula XIII

To a solution of the appropriate compound formula XIII (0.33 mmol) in dry ether (10 ml) cooled to −30° C. under argon methyl lithium (0.45 ml, 1.6 M in ether) is added. The reaction mixture is slowly heated to room temperature during 2 hours and then diluted with ether (15 ml). The ether phase is extracted with water (3×5 ml) and saturated aqueous sodium chloride (5 ml), dried and evaporated in vacuo to yield a crude product. This is purified by chromatography (mixture of ether and pet. ether as eluant) to give the title compound of the preparation.

General Procedure 12

Deprotection of a Compound of Formula III with PPTS

To a solution of the appropriate compound III (0.16 mmol) in 99% ethanol (2 ml) PPTS (2 mg) is added, and the mixture is stirred at 50° C. under argon for one hour. Ethyl acetate ( 15 ml) is added and the mixturre extracted with saturated aqueous $NaHCO_3$ (3×5 ml) and water (5 ml). The organic phase is dried and evaporated in vacuo to yield a crude product, which is purified by chromatography to give the desired compound.

Preparations

Preparation 1

Compound 3

Method: General Procedure 1
Starting Material: Methyl 4-iodobenzoate
$^1$H NMR: δ=7.66 (m, 2H), 7.24 (m, 2H), 1.72 (s, 1H), 1.55 (s, 6H) ppm Preparation 2

Compound 4

Method: General Procedure 1
Starting Material: Methyl 3-iodobenzoate
$^1$H NMR: δ=7.85(t, 1H), 7.57(dd, 1H), 7.41(dd, 1H), 7.07(t, 1H), 1.56(s, 6H) ppm Preparation 3

Compound 5

Method: General Procedure 2
Starting Material: Compound 3
$^1$H NMR: δ=7.65 (m, 2H), 7.20 (m, 2H), 4.42 (m, 1H), 3.95 (m, 1H), 3.39 (m, 1H), 1.83 (m, 1H), 1.70–1.35 (m, 5H), 1.63 (s, 3H), 1.49 (s, 3H) ppm Preparation 4

Compound 6

Method: General Procedure 2
Starting Material: Compound 4
$^1$H NMR: δ=7.79 (t, 1H), 7.58 (dd, 1H), 7.42 (dd, 1H), 7.07 (t, 1H), 4.44 (m, 1H), 3.95 (m, 1H), 3.40 (m, 1H), 1.84 (m, 1H), 1.72–1.35 (m, 5H), 1.63 (s, 3H), 1.49 (s, 3H) ppm Preparation 5

Compound 7

Method: General Procedure 3
Starting Material: Compound 3
$^1$H NMR: δ=7.62 (m, 2H), 7.18 (m, 2H), 1.54 (s, 6H), 0.09 (s, 9H) ppm Preparation 6

Compound 42

Method: General Procedure 7
Starting Material: 4-(2-hydroxy-2-propyl)-phenylmethyl-triphenylphosphonium bromide.
$^1$H NMR: δ=7.42 (m, 2H), 7.23 (m, 2H), 6.41 (d, 1H), 6.24 (d, J=11.8 Hz, 1H), 5.76 (d, 1H), 5.53 (m, 1H), 4.96 (m, 1H), 4.91 (m, 1H), 4.50 (m, 1H), 4.19 (m, 1H), 2.83 (m, 1H), 2.67 (m, 1H), 2.49 (dd, 1H), 2.30 (d, 1H), 2.09–1.01 (m, 14H), 1.57 (s, 6H), 1.07 (d, 3H), 0.88 (s, 9H), 0.82 (s, 9H), 0.19 (s, 3H), 0.05 (s, 3H), 0.04 (s, 3H), 0.03 (s, 3H), 0.01 (s, 3H) ppm Preparation 7

Compound 43

Method: General Procedure 6
Starting Material: Compound 42
$^1$H NMR: δ=7.42 (m, 2H), 7.23 (m, 2H), 6.21 (m, 2H), 5.95 (d, 1H), 5.53 (m, 1H), 5.15 (m, 1H), 4.81 (m, 1H), 4.35 (m, 1H), 4.16 (m, 1H), 2.78 (m, 1H), 2.66 (m, 1H), 2.41 (dd, 1H), 1H), 2.19 (dd, 1H), 2.07–1.00 (m, 14H), 1.57 (s, 6H), 1.07 (d, 3H), 0.86 (s, 9H), 0.86 (s, 9H), 9H), 0.19 (s, 3H), 0.04 (m, 12H) ppm Preparation 8

Compound 44

Method: General Procedure 4
Starting Material: Compound 5
$^1$H NMR: δ=7.33 (m, 4H), 6.45 (d, 1H), 5.84 (d, 1H), 4.99 (m, 1H), 4.94 (m, 1H), 4.53 (m, 1H), 4.38 (dd, 1H), 4.22 (m, 1H), 3.94 (m, 1H), 3.36 (m, 1H), 2.89 (m, 1H), 2.72 (m, 1H), 1H), 2.55 (dd, 1H), 2.32 (m, 1H), 2.15–1.22 (m, 19H), 1.64 (s, 3H), 1.48 (s, 3H), 1.29 (d, 3H), 0.90 (s, 9H), 0.86 (s, 9H), 0.64 (s, 3H), 0.06 (m, 12H) ppm Preparation 9

Compound 45

Method: General Procedure 12
Starting Material: Compound 44
$^1$H NMR: δ=7.35 (m, 4H), 6.23 (d, 1H), 6.02 (d, 1H), 5.18 (m, 1H), 4.86 (m, 1 H), 4.36 (m, 1H), 4.18 (m, 1H), 2.84 (m, 1H), 2.70 (m, 1H), 2.44 (dd, 1H), 2.21 (dd, 1H), 2.12–1.14 (m, 14H), 1.55 (s, 6H), 1.28 (d, 3H), 0.87 (s, 9H), 0.86 (s, 9H), 0.61 (s, 3H), 0.05 (m, 12H) ppm Preparation 10

Compound 46

Method: General Procedure 5
Starting Material: Compound 45
$^1$H NMR: δ=7.44 (m, 2H), 7.26 (m, 2H), 6.44 (d, 1H), 6.25 (d, J=11.8 Hz, 1H), 5.78 (d, 1H), 5.45 (m, 1H), 4.98 (m, 1H), 4.92 (m, 1H), 4.52 (m, 1H), 4.19 (m, 1H), 2.81 (m, 2H), 2.50 (dd, 1H), 2.30 (m, 1H), 2.10–1.02 (m, 14H), 1.59 (s, 6H), 1.13 (d, 3H), 0.89 (s, 9H), 0.84 (s, 9H), 0.50 (s, 3H), 0.06 (s, 3H), 0.05 (s, 3H), 0.04 (s, 3H), 0.03 (s, 3H) ppm Preparation 11

Compound 47

Method: General Procedure 6

Starting Material: Compound 46

$^1$H NMR: δ=7.44 (m, 2H), 7.25 (m, 2H), 6.23 (d, J=11.7 Hz, 1H), 6.21 (d, 1H), 5.98 (d, 1H), 5.45 (m, 1H), 5.16 (m, 1H), 4.83 (m, 1H), 4.36 (m, 1H), 4.18 (m, 1H), 2.81 (m, 2H), 2.42 (dd, 1H), 2.20 (dd, 1H), 2.07–1.02 (m, 14H), 1.59 (s, 6H), 1.13 (d, 3H), 0.87 (s, 9H), 0.86 (s, 9H), 0.50 (s, 3H), 0.05 (m, 12H) ppm Preparation 12

Compound 48

Method: General Procedure 7

Starting Material: 3-Ethoxycarbonylphenylmethyl-triphenylphosphonium bromide.

$^{13}$C NMR: δ=166.9, 153.3, 142.8, 140.2, 138.1, 135.2, 132.7, 129.9, 129.6, 128.0, 127.2, 124.9, 121.5, 116.3, 106.6, 70.1, 67.0, 56.8, 56.2, 51.9, 45.6, 43.7, 40.3, 36.4, 34.6, 28.7, 27.0, 25.6, 25.6, 23.3, 22.0, 20.3, 18.0, 17.9, 12.1, −4.9, −5.0, −5.1 ppm Preparation 13

Compound 49

Method: General Procedure 6

Starting Material: Compound 48

$^1$H NMR: δ=7.93(t, 1H), 7.88(m, 1H), 7.44(m, 1H), 7.38(t, 1H), 6.28(d, 1H, J=11.4Hz), 6.19(d, 1H), 5.97(d, 1H), 5.52(t, 1H, J=11.4 Hz), 5.16(m, 1H), 4.82(m, 1H), 4.35 (m, 1H), 4.17(m, 1H), 3.90(s, 3H), 2.76(m, 2H), 2.41(dd, 1H), 2.2(dd, 1H), 2.03–0.71 (m, 13H), 1.13(d, 3H), 0.87(s, 9H), 0.85(s, 9H), 0.47(s, 3H), 0.03(m, 12H) ppm Preparation 14

Compound 50

Method: General Procedure 11

Starting Material: Compound 49

$^1$H NMR: δ=7.38(t, 1H), 7.31(m, 2H), 7.15(m, 1H), 6.28(d, 1H, J=11.5 Hz), 6.20 (d, 1H), 5.97(d, 1H), 5.47(t, 1H, J=11.5 Hz), 5.15(m, 1H), 4.82(m, 1H), 4.35(m, 1H), 4.17 (m, 1H), 2.80(m, 2H), 2.42(dd, 1H), 2.20(dd, 1H), 2.08–0.70(m, 14H), 1.58(s, 3H), 1.57(s, 3H), 1.12(d, 3H), 0.86(s, 9H), 0.85(s, 9H), 0.47(s, 3H), 0.04(m, 12H) ppm Preparation 15

3-Ethoxycarbonylphenylmethyl-triphenylphosphonium bromide

Method: General Procedure 8

Starting Material: Ethyl 3-bromomethylbenzoate $^1$H NMR: δ=7.90(m, 17H), 7.60(t, 1H), 7.25(t, 1H), 5.55(d, 2H), 4.24(q, 2H), 1.29(t, 3H) ppm Preparation 16

4-(2-Hydroxy-2-propyl)-phenylmethyl-triphenylphosphonium bromide

Method: General Procedure 8

Starting Material: 2-(4-Bromomethylphenyl)-2-propanol $^1$H NMR: δ=7.88(m, 3H), 7.72–7.60(m, 12H), 7.32(d, 2H), 6.95(dd, 2H), 4.90(d, 2H), 1.48(s, 6H) ppm Example 1

1(S), 3 (R)-Dihydroxy-20(R)-[2(Z)-(3-(2-hydroxy-2-propyl)-phenyl)-vinyl]-9,10-secopregna-5(Z), 7(E), 10(19)-triene Method: General Procedure 10

Starting Material: Compound 50

$^{13}$C NMR: δ=148.9, 147.6, 142.8, 139.3, 137.9, 133.1, 128.1, 126.8, 126.2, 124.9, 124.8, 1.22.4, 117.1, 111.7, 72.5, 70.7, 66.8, 56.9, 56.3, 45.9, 45.2, 42.8, 40.4, 34.9, 31.8, 31.7, 29.0, 27.3, 23.6, 22.3, 20.5, 12.4 ppm Example 2

1(S), 3(R)-Dihydroxy-20(S)-[2(Z)-(4-(2-hydroxy-2-propyl)-phenyl)-vinyl]-9,10-secopregna-5(Z), 7(E), 10(19)-triene Method: General Procedure 10

Starting Material: Compound 43

$^1$H NMR: δ=7.42 (m, 2H), 7.23 (m, 2H), 6.33 (d, 1H), 6.24 (d, J=11.4 Hz, 1H), 5.95 (d, 1H), 5.53 (m, 1H), 5.28 (m, 1H), 4.94 (m, 1H), 4.40 (m, 1H), 4.19 (m, 1H), 2.88–2.50 (m, 3H), 2.28 (dd, 1H), 2.08–1.04 (m, 16H), 1.58 (s, 6H), 1.07 (d, 3H), 0.21 (s, 3H) ppm Example 3

1(S), 3(R)-Dihydroxy-20(R)-[2(Z)-(4-(2-hydroxy-2-propyl)-phenyl)-vinyl]-9,10-secopregna -5(Z) 7(E), 10(19)-triene Method: General Procedure 9

Starting Material: Compound 47

$^1$H NMR: δ=7.43 (m, 2H), 7.23 (m, 2H), 6.36 (d, 1H), 6.24 (d, J=11.4 Hz, 1H), 5.98 (d, 1H), 5.53 (m, 1H), 5.28 (m, 1H), 4.96 (m, 1H), 4.40 (m, 1H), 4.19 (m, 1H), 2.88–2.50 (m, 3H), 2.28 (dd, 1H), 2.08–1.04 (m, 16H), 1.59 (s, 6H), 1.12 (d, 3H), 0.51 (s, 3H) ppm Example 4

Capsules Containing Compound 101

Compound 101 was dissolved in arachis oil to a final concentration of 1 µg of Compound 101/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 101 in oil solution, such that each capsule contained 0.1 µg of Compound 101.

Example 5

Dermatological Cream Containing Compound 101

In 1 g almond oil was dissolved 0.05 mg of Compound 101. To this solution was added 40 g of mineral oil and 20 g of self-emulsifying beeswax. The mixture was heated to liquify. After the addition of 40 ml hot water, the mixture was mixed well. The resulting cream contains approximately 0.5 µg of Compound 101 per gram of cream.

Example 6

Injectable Solution Containing Compound 101

A solution useful for injections containing
10 µg of compound No. 101 herein
15.4 mg disodium phosphate dihydrate
2 mg sodium dihydrogen phosphate dihydrate
0.8 mg sodium chloride
5 mg sodium ascorbate
5 mg Solutol® HS 15
ad 1 ml water for injection.

What is claimed is:

1. A compound of the formula I

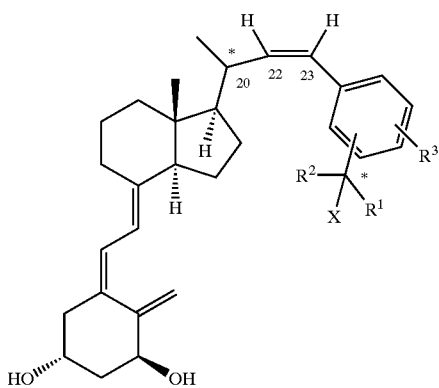

wherein X represents hydrogen or hydroxy; $R^1$ and $R^2$, which may be the same or different, represent hydrogen, $(C_1-C_4)$alkyl optionally substituted with one hydroxyl group or one or more fluorine atoms, or, together with the carbon atom to which they are attached, $R^1$ and $R^2$ form a $(C_3-C_5)$carbocyclic ring; $R^3$ represents hydrogen, $(C_1-C_4)$alkyl, $(C_1-C_4)$alkoxy, fluorine, chlorine, bromine, or iodine, and in-vivo hydrolyzable esters thereof with pharmaceutically acceptable acids.

2. A compound according to claim 1 wherein X represents hydroxy.

3. A compound according to claim 1 or 2 wherein the starred carbon atom other than the carbon atom No. 20 is achiral.

4. A compound according to claim 3 wherein $R^1$ and $R^2$ are the same and represent methyl or ethyl, optionally substituted with one hydroxyl group or one or more fluorine atoms.

5. A compound according to claim 4 wherein $R^1$ and $R^2$ both represent trifluoromethyl or ethyl substituted with one hydroxyl group.

6. A compound according to claim 1 or 2 in the form of diastereoisomers of a compound of formula I in pure form or as a mixture of diastereoisomers.

7. The compound according to claim 1, wherein the configuration of the carbon atoms marked with an asterisk may be R or S.

8. A compound according to claim 1 or 2, wherein the configuration at carbon atom No. 20 is R or S.

9. A compound according to claim 1, which is selected from the group consisting of:

1(S), 3(R)-Dihydroxy-20(R)-[2(Z)-(3-(2-hydroxy-2-propyl)-phenyl)-vinyl]9, 10-secopregna-5(Z), 7(E), 10(19)-triene;

1(S), 3(R)-Dihydroxy-20(S )-[2(Z)-(4-(2-hydroxy-2-propyl)-phenyl)-vinyl]-9,10-secopregna-5(Z), 7(E), 10(19)-triene; and 1(S), 3(R)-Dihydroxy-20(R)-[2(Z)-(4-(2-hydroxy-2-propyl)-phenyl)-vinyl]9,10-secopregna-5(Z), 7(E), 10(19)-triene.

10. A pharmaceutical composition containing an effective amount of a compound according to claim 1 or 2 together with pharmaceutically acceptable carriers and/or excipients.

11. A pharmaceutical composition according to claim 10 in dosage unit form.

12. The pharmaceutical composition according to claim 11, wherein said dosage unit comprises from 0.05–100 mg of the compound of formula I.

13. The compound according to claim 3, wherein tho configuration at carbon atom No. 20 is R or S.

14. The pharmaceutical composition according to claim 12, wherein said dosage unit comprises from 0.1–50 mg of the compound of formula I.

* * * * *